United States Patent [19]

Ohlinger et al.

[11] 4,061,726
[45] Dec. 6, 1977

[54] MANUFACTURE OF ACICULAR γ-IRON(III) OXIDE

[75] Inventors: Manfred Ohlinger, Frankenthal; Eduard Schöenafinger, Ludwigshafen; Guenter Vaeth, Limburgerhof; Heinz Stritzinger, Ludwigshafen; Eberhard Köester, Frankenthal; Hans Henning Schneehage; Werner Steck, both of Mutterstadt, all of Germany

[73] Assignee: BASF Aktiengesellschaft, Ludwigshafen, Germany

[21] Appl. No.: 732,901

[22] Filed: Oct. 15, 1976

[30] Foreign Application Priority Data

Nov. 8, 1975 Germany .............................. 2550308

[51] Int. Cl.² .............................................. C01G 49/02
[52] U.S. Cl. ..................................... 423/634; 423/633
[58] Field of Search ............... 423/633, 634, 140, 142, 423/151, 152

[56] References Cited

U.S. PATENT DOCUMENTS

| | | |
|---|---|---|
| 3,845,198 | 10/1974 | Marcot .................................. 423/634 |
| 3,912,646 | 10/1975 | Leitner et al. ........................ 423/634 |
| 3,947,502 | 3/1976 | Leitner et al. ........................ 423/634 |

*Primary Examiner*—Earl C. Thomas
*Assistant Examiner*—Wayne A. Lange
*Attorney, Agent, or Firm*—Keil, Thompson & Shurtleff

[57] ABSTRACT

Goethite is obtained by reacting an aqueous solution of an iron (II) salt with an aqueous solution of an alkali metal hydroxide and oxidizing the resulting iron(II) hydroxide. The oxidation is carried out in three stages. In the first stage, from 4 to 15% by weight are oxidized in the course of from 0.4 to 5 hours, in the second stage from 60 to 85% by weight are oxidized in the course of from 1.5 to 6 hours and in a third stage the remaining amount of iron is oxidized.

6 Claims, No Drawings

MANUFACTURE OF ACICULAR γ-IRON(III) OXIDE

The present invention relates to a process for the manufacture of acicular goethite (alpha-FeOOH).

Acicular goethite is an important starting material for the manufacture of acicular gamma-iron(III) oxide by dehydrating the goethite to alpha-Fe$_2$O$_3$, reducing the alpha-Fe$_2$O$_3$ to magnetite (Fe$_3$O$_4$) and subsequently oxidizing the magnetite with oxygen-containing gases to gamma-iron(III) oxide, which is employed as a magnetizable pigment in the manufacture of magnetic recording media.

Recently, magnetic recording media which contain acicular metallic iron as the magnetic pigment, in place of acicular gamma-iron(III) oxide, have also been manufactured. The advantages of this metallic pigment over oxide magnetic pigments are, above all, a substantially increased residual induction and, as a result, a substantially increased playback signal level or, at a given playback signal level, an increased recording density compared to that obtained with oxide magnetic pigments. The metallic iron pigments can be manufactured in various ways, e.g. by deposition on a mercury cathode, by reduction of iron salts with hydrides, by vacuum vaporization of the metal and subsequent deposition as whiskers, or, above all, by reduction of iron oxides with gaseous reducing agents, especially hydrogen.

The electro-acoustic properties of both the gamma-iron(III) oxide and of the metallic iron are decisively influenced by the size and shape of the particles and these in turn depend on the particular starting material used. If goethite is used as the starting material for the manufacture of the above magnetic pigments, it means that the electro-acoustic properties of the said pigments will be influenced, from the start, by the geometrical shape and crystal size of the goethite.

Goethite can be manufactured by two conventional methods, namely an acid process or an alkaline process.

The acid process is carried out in two stages; in a first stage nuclei of goethite are manufactured in acid suspension, by oxidation, from iron(II) sulfate, and in a second stage further goethite is formed from the suspension, in the presence of metallic iron, by oxidation, this further material growing onto the nuclei formed in the first stage. This process has the disadvantage of a low space-time yield and of giving goethite which does not have a very pronounced acicular character. However, the process has the advantage that the reaction can be discontinued when a certain particle size is reached. In the case of the alkaline process, also carried out on an industrial scale, iron(II) hydroxide is first precipitated from an iron(II) salt solution by reaction with an excess amount of caustic alkali solution, and this hydroxide is then converted to goethite by passing oxygen-containing gases into the mixture. This process has the advantage, over the acid process, that the space-time yield is from about 5 to 10 times greater, that the goethite formed has a pronounced acicular character with a length to width ratio of from 15 to 20 : 1, and that the coercive force of the magnetic pigment manufactured therefrom is higher than that of the magnetic pigments obtained from goethite manufactured by the acid process. It is a disadvantage, however, that the size of the particles can only be controlled incompletely, since the reaction can only be discontinued when all the iron(II) hydroxide first precipitated has been oxidized, since otherwise the magnetic and electro-acoustic properties of the gamma-iron(III) oxide or metallic iron manufactured therefrom are adversely affected. However, a deliberate control of the particle size and hence of the surface area would be very desirable, since it would permit selection of the optimum properties of the magnetic pigment to be manufactured, in accordance with the intended use of the magnetic recording medium.

In order to be able to reduce the disadvantages of the alkaline process and in particular to reduce the reaction time, it has been disclosed to stir the iron hydroxide suspension in an inert atmosphere before oxidizing the suspension. It has been disclosed that fine goethite crystals can be obtained by dispersing the iron(II) salt solution in the alkali metal hydroxide solution, in the absence of an oxidizing agent, in such a way that there is virtually no local excess of iron(II) salt. Furthermore, the final dispersion obtained should have a goethite concentration of less than 15 g/l and a dissolved alkali metal hydroxide concentration of less than 60 g/l. After oxidation, the resulting goethite dispersion should be heated to the boil to complete the crystallization. It is true that these conventional measures to some extent influence the pigment properties of the goethite and of the gamma-iron(III) oxide and/or metallic iron manufactured therefrom, but it is impossible to achieve a uniform and constant product quality with them.

It is an object of the present invention to provide a process for the manufacture of goethite by reacting an aqueous solution of an iron(II) salt with an aqueous solution of an alkali metal hydroxide and oxidizing the suspension of iron(II) hydroxide, thus obtained, with oxygen or oxygen-containing gases to give goethite, which process gives a product which is uniform in respect of size and crystal shape.

We have found that this object is achieved if the oxidation of the iron(II) hydroxide suspension is carried out in three stages in such a way that in a first stage from 4 to 15% by weight of the amount of iron(II) present are oxidized in the course of from 0.4 to 5 hours, in a second stage from 60 to 85% by weight of the amount of iron(II) originally present are oxidized in the course of from 1.5 to 6 hours and in a third stage the remaining amount of iron is oxidized.

It is essential that the oxidation of the iron(II) hydroxide should initially take place slowly and that the rate should gradually be increased during the reaction, for example by increasing the feed of the oxidizing gas. Thus, not more than 15% by weight of the total amount of iron present in the suspension should be oxidized in the first stage, which takes from 0.4 to 5 hours. Preferably, from 6 to 12% of the amount of iron(II) contained in the suspension are oxidized in the first stage, in the course of from 2 to 4 hours. The oxidation can be started during the actual precipitation of the iron(II) hydroxide; however, to achieve a particularly uniform quality of product, it is more advantageous only to start the oxidation as soon as possible after the precipitation, which is then carried out under an inert gas atmosphere. This slow oxidation can be carried out by causing a turbulent motion, for example by stirring, of the suspension of the iron(II) hydroxide which, at the surface, is in contact with an oxygen-containing gas, e.g. the atmosphere. As a rule it is not necessary to pass an oxygen-containing stream of gas through the suspension.

In the second stage, the rate of oxidation is increased in such a way that from 60 to 85% by weight of the amount of iron(II) originally contained in the suspension is oxidized to trivalent iron over a period of from 1.5 to 6 hours. To increase the rate of oxidation, an oxygen-containing gas, e.g. air or oxygen, or oxygen diluted with an inert gas, e.g. nitrogen, is introduced into the suspension whilst continuing the stirring. Advantageously, the rate of oxidation is also increased during this stage, by increasing the feed of oxygen-containing gas through initially introducing from 0.3 to 0.9 mole of oxygen per hour per gram atom of the iron contained in the suspension and increasing this amount of oxygen continuously or stepwise to from 0.7 to 1.5 moles, up to the end of the second stage. Preferably, the second stage of the oxidation is carried out in the course of from 2 to 5 hours. Preferably, from 0.4 to 0.7 mole of oxygen per gram atom of the iron contained in the suspension are introduced per hour at the beginning of the second stage, and this amount of oxygen is increased, up to the end of the second stage, to from 0.8 to 1.1 moles of oxygen per gram atom of iron per hour. As a result of the slow and gradually increasing rate of oxidation up to the end of the second stage, a uniform formation of goethite nuclei commences and as a result, at the end of the entire oxidation stage, a goethite of uniform crystal size and shape and with geometrical dimensions of good reproducibility is obtained.

In the third stage, the oxidation of the remaining iron(II) hydroxide is completed. Here, the rate of oxidation is not so critical and it is therefore possible to increase the rate substantially in order to increase the space-time yield. For this reason, from 1.5 to 2.5 moles of oxygen, preferably from 1.8 to 2.1 moles of oxygen, per gram atom of the iron contained in the suspension can be introduced into the latter per hour, in the third stage.

The iron(II) hydroxide suspensions to be oxidized in accordance with the invention are conventionally obtained by precipitating iron(II) salt solution, e.g. iron sulfate, iron chloride or iron nitrate, with alkali metal hydroxide solutions, e.g. solutions of NaOH or KOH, which are employed in from two-fold to five-fold excess over the stoichiometrically required amount. The suspensions obtained in this way usually contain from 2.5 to 10% by weight of iron(II) hydroxide. The oxidation is advantageously carried out at from 10° to 30° C. The reaction is carried out, for example, in a stirred kettle into the lower part of which the oxygen-containing gases are introduced, and distributed over the entire cross-section, in order to achieve very uniform distribution.

The goethite crystals obtained in accordance with the process of the invention are next dehydrated, if appropriate, by conventional methods at from 150° to 190° C to give alpha-iron(III) oxide, before being reduced with reducing gases, e.g. hydrogen, at from 350° to 500° C, go give magnetite, which is then oxidized in the presence of oxygen or oxygen-containing gases, e.g. air, at from 150° to 250° C, to give acicular gamma-iron(III) oxide.

To manufacture acicular metallic iron, the goethite can either be directly treated with reducing gases, e.g. hydrogen, at from 250° to 400° C or the goethite is first dehydrated to alpha-iron(III) oxide.

Of course, gamma-iron(III) oxides modified with foreign elements, e.g. with cobalt or manganese, can also be manufactured by the process according to the invention. These elements can be introduced at any desired stage, e.g. by admixing salts of the foreign elements to the iron salt solutions when manufacturing the iron(III) oxide or subsequently applying the foreign elements to the surface of the goethite.

The magnetic pigments — both gamma-iron(III) oxide and metallic iron — manufactured according to the invention have a very uniform particle size. This uniformity results from the fact that the goethite, which has a surface area (measured by the BET method) of from 60 to 95 m$^2$/g, has a very narrow particle spectrum. When using the gamma-iron(III) oxide, extremely low-noise tapes and sub-layers — in multi-layer tapes — of low coercive force can be produced, whilst when using the metallic iron obtained, tapes with substantially increased playback signal level or, for the same playback signal level as when using gamma-iron(III) oxide pigments, tapes with substantially higher recording density can be produced.

To manufacture magnetic coatings, the gamma-iron(III) oxide obtained from the goethite manufactured according to the invention is dispersed by conventional methods in polymeric binders. Suitable binders for this purpose are conventional compounds, e.g. homopolymers and copolymers of vinyl derivatives, polyurethanes, polyesters and the like. The binders are used in solutions in suitable organic solvents, which may contain further additives, e.g. to increase the conductivity and abrasion resistance of the magnetic coatings. On milling the magnetic pigment, the binder and any additives, a homogeneous dispersion is obtained, which is applied to rigid or flexible bases such as films, sheets or cards. The magnetic particles contained therein are oriented by a magnetic field and the coating is then solidified by drying.

The acicular metallic iron is also processed by a similar method to that just described. However, in the case of metallic iron, special protective measures must be taken, e.g. the process must be carried out under an inert gas atmosphere unless the pigment, which is usually pyrophoric, has been passivated beforehand by suitable conventional measures. In contrast to the use of gamma-iron(III) oxide, the addition of conductive adjuvants, when manufacturing magnetic recording media for any applications, can be dispensed with, since metallic iron itself is highly conductive.

In the Examples, parts and percentages are by weight, unless stated otherwise.

EXAMPLE 1

19.4 kg of 15% strength sodium hydroxide solution are first introduced into a 30 l stirred kettle. 4.2 kg of 30.5% strength FeCl$_2$ solution are added, whilst stirring. The resulting Fe(OH)$_2$ suspension is stirred vigorously for 3.5 hours in air at 18° C, during which time the Fe$^{++}$ concentration falls by 7.5% from an initial value of 0.556 mole of Fe$^{++}$/l (10 ml of suspension consume 48.9 ml of N/10 KMnO$_4$ solution) to 0.514 mole of Fe$^{++}$, corresponding to the consumption of 45.2 ml of KMnO$_4$ solution. 535 l of air are then passed in in the course of 1 hour (corresponding to 0.5 mole of oxygen/gram atom of Fe).

During the next hour, the amount of air is increased to 749 l (0.7 mole of oxygen/gram atom of iron). The amount of air is increased to 856 l (0.8 mole of oxygen/gram atom of iron) in the third hour and to 963 l (0.9 mole of oxygen/gram atom of Fe) in the fourth hour. During the period from the second hour to the fourth hour inclusive, the Fe$^{++}$ content of the solution has decreased by 71%. From the fifth hour onward, 1,606 l of air (1.5 moles of oxygen/gram atom of Fe) are passed in per hour. During this time, the temperature is kept constant at 18° C. After a further 3 hours, the oxidation has ended. The acicular goethite is filtered off, washed and dried. The yield is 900 g of goethite having a surface area of 69 m²/g, measured by the BET method, and having a tap density of 0.51 g/cm³.

EXAMPLE 2

19.2 kg of 12% strength sodium hydroxide solution are first introduced into a 40 l kettle, 8.2 kg of 19% strength $FeSO_4$ solution are added, whilst stirring. The resulting $Fe(OH)_2$ suspension is stirred vigorously at 20° C in air until, after 3 hours, the concentration of iron(II) has fallen from 0.436 mole/l to 0.385 mole/l (corresponding to a decrease of 11.8%).

637 l of air (corresponding to 0.6 mole of oxygen/gram atom of Fe) are now passed in in the course of 1 hour, whilst stirring constantly. The amount of air passed in is raised after each hour by 159 l of air, so that after a total of 4 hours it has reached 1,114 l/hour (1.05 moles of oxygen/gram atom of Fe). Air is passed in at this rate for 1 hour. After the fourth hour, the $Fe^{++}$ content of the solution has decreased by a total of 62%. From the fifth hour onward, the amount of air is increased to 1,699 l/hour (1.6 moles of oxygen/gram atom of Fe). The oxidation has ended after a further 4 hours. During the entire course of the oxidation, the contents of the kettle are kept at 20° C and stirred. The acicular goethite is filtered off, washed and dried. The yield is 900 g of goethite having a surface area of 75 m²/g measured by the BET method. The tap density is 0.55 g/cm³.

COMPARATIVE EXAMPLE A 19.4 kg of 15% strength sodium hydroxide solution are first introduced into a 30 l stirred kettle, as in Example 1. 4.2 kg of 30.5% strength $FeCl_2$ solution are added, whilst stirring. When the precipitation of $Fe(OH)_2$ has ended, 1,500 l of air/hour (1.4 moles of oxygen/gram atom of Fe) are passed into the suspension and the temperature is kept at 18° C. after 7.5 hours, the entire iron(II) hydroxide has been oxidized to goethite. The surface area, measured by the BET method, of the acicular pigment is 77 m²/g and the tap density is 56 g/cm³.

COMPARATIVE EXAMPLE B 19.4 kg of 15% strength sodium hydroxide solution are first introduced into a 30 l stirred kettle, as in Example 1. 4.2 kg of 30.5% strength $FeCl_2$ solution are added, whilst stirring. When the precipitation of $Fe(OH)_2$ has ended, 535 l of air/hour (0.5 mole of oxygen/gram atom of Fe) are passed into the suspension at 18° C. After 16 hours, the entire iron(II) hydroxide has been oxidized to goethite. The surface area, measured by the BET method, of the acicular pigment is 43 m²/g and the tap density is 0.41 g/cm³.

EXAMPLE 3

19.4 kg of 15% strength sodium hydroxide solution are first introduced into a 30 l stirred kettle. 8.2 kg of 19% strength $FeSO_4$ solution, in which 34 g of cobalt chloride ($CoCl_2 \cdot 6 H_2O$) and 6.7 g of manganese sulfate ($MnSO_4 \cdot 4 H_2O$) are dissolved, are added whilst stirring. The resulting suspension is processed further as described in Example 1. The resulting acicular goethite, modified with 1.5% of Co and 0.3% of Mn, has a surface area, measured by the BET method, of 67.5 m²/g and a tap density of 0.50 g/cm³.

EXAMPLE 4

450 g of goethite from Example 1 are suspended in 10 l of $H_2O$, with vigorous stirring. 12.5 g of cobalt chloride and 1.8 g of manganese sulfate dissolved in 1.0 l of water are then added. The pH is brought to 7 by means of dilute sulfuric acid, whilst stirring. It is then raised to 9 by means of ammonia. The product is then filtered off, washed and dried at 200° C.

COMPARATIVE EXAMPLE C

Following the method described in Example 4, goethite from Comparative Example A is encapsulated in cobalt hydroxide and manganese hydroxide, filtered off and dried at 200° C.

The table which follows gives some characteristic measurements on the goethite obtained as described in Examples 1 to 4 and A to C:

| Example | 1 | 2 | A | B | 3 | 4 | C |
|---|---|---|---|---|---|---|---|
| Tap density g/cm³ | 0.51 | 0.55 | 0.56 | 0.41 | 0.51 | as 1 | as A |
| BET surface area, m²/g | 69 | 75 | 77 | 43 | 67.5 | " | " |
| Average needle length (μ) | 0.35 | 0.3 | 0.3 | 0.6 | 0.35 | " | " |
| Needle length from/to (μ) | 0.3/0.4 | 0.25/0.35 | 0.2/0.6 | 0.3/0.8 | 0.3/0.4 | " | " |
| Length to width ratio | 15:1 | 15:1 | 10:1 to 18:1 | 12:1 to 17:1 | 15:1 | " | " |

As can be seen from this table, the goethite obtained by the process according to the invention, in accordance with Examples 1 to 4, is distinguished by a narrower particle size spectrum, shown by the values of the needle length and of the length to width ratio.

EXAMPLE 5

Conversion of the goethite, obtained as described in the previous Examples, to magnetic gamma-iron(III) oxide The goethite pigments obtained as described in Examples 1 to 4 and Comparative Examples A, B and C are reduced by the same conventional method in a fluidized bed furnace at 400° C, in a hydrogen atmosphere, to give magnetite, and the latter is then re-oxidized in a stream of air, at from 200° to 250° C, to give gamma-iron(III) oxide. After compression to a tap density of 0.85 g/cm³, the pigments have the magnetic properties and specific surface areas shown in the table below.

| Powder values Example | 1 | 2 | A | B | 3 | 4 | C |
|---|---|---|---|---|---|---|---|
| $H_c$ (Oe) | 300 | 295 | 265 | 290 | 380 | 365 | 365 |
| Specific remanence (nTm³/g) | 41.5 | 41.7 | 40.5 | 42.1 | 42.3 | 41.9 | 40.6 |
| BET surface area (m²/g) | 20.3 | 22.1 | 23.2 | 16.5 | 20.5 | 20.3 | 23.2 |

Magnetic recording media, using a polyethylene terephthalate film as the base, are manufactured by the same conventional method from the gamma-$Fe_2O_3$ pigments obtained from the goethite manufactured according to the process of the invention, and from the pigments obtained according to Comparative Examples A to C. To produce the magnetic coating, the pigments are dispersed, in each case under identical conditions, in a partially hydrolyzed vinyl chloride/vinyl acetate copolymer to which a mixture of equal parts by volume of tetrahydrofuran and toluene has been added, and the dispersion is applied to the base film and dried. The thickness of the magnetic coating is in each case about 6μ, the film being 12μ thick and the tape 3.81 mm wide.

The magnetic and electro-acoustic properties are determined on magnetic tapes, all of which have been manufactured identically, and are listed in the table which follows (the last-mentioned property having been measured in accordance with DIN 45,412, sheet 2, at a speed of 4.75 cm/sec. against reference tape C 521-V).

| Tape values Pigments from Examples | 1 | 2 | A | B | 3 | 4 | c |
|---|---|---|---|---|---|---|---|
| Relative bias current (dB) | 0 | 0 | 0 | 0 | +0.6 | +0.6 | +0.6 |
| $H_c$ (Oe) | 305 | 300 | 275 | 295 | 382 | 373 | 375 |
| Remanence (mT) in the preferred direction | 12.9 | 13.2 | 12.5 | 11.3 | 12.1 | 12.4 | 10.9 |
| Orientation ratio | 1.90 | 1.94 | 1.65 | 1.52 | 1.79 | 1.82 | 1.47 |
| Sensitivity (dB) | −0.3 | −0.5 | −1.1 | −0.3 | +0.5 | +0.7 | −0.8 |
| Frequency response (dB) | +2.5 | +2.3 | +0.4 | −0.7 | +3.1 | +2.8 | +1.6 |
| Distortion ratio (dB) | 0 | +0.2 | −0.5 | +0.4 | +0.3 | +0.5 | −1.0 |
| Relative reference level to bias noise ratio (dB) | +4.2 | +4.5 | +1.0 | −0.4 | +4.4 | +3.9 | +0.9 |
| Relative maximum output level to bias noise ratio (dB) | +3.9 | +4.0 | −0.1 | −0.7 | +4.9 | +4.6 | +0.1 |

The increase in the relative maximum output level to bias noise ratio relative to Comparative Examples A, B and C is shown by Examples 1, 2, 3 and 4. This increase results from the sensitivity (maximum output level) and the excellent relative reference level to bias noise ratios; the frequency response is also substantially improved. These improved values are due to the magnetic pigment consisting of fine, small needles and having a very uniform particle size spectrum.

EXAMPLE 6

The goethite pigments obtained as described in Examples 1 and 2 and Comparative Examples A and B are treated with barium acetylacetonate to prevent sintering and then reduced to acicular metallic iron for about 7 hours in a stream of hydrogen at 300° C. The pyrophoric material is stabilized by careful oxidation of the surface. The following values are subsequently measured on the powder:

| Example | 1 | 2 | A | B | |
|---|---|---|---|---|---|
| $H_c$ (Oe) | 900 | 965 | 580 | 720 | Magnetic measurements carried out at 160 kAm |
| Specific remanence (nTm³/g) | 81 | 75 | 63 | 58 | |
| BET surface area (m²/g) | 28 | 32 | 23 | 22 | |

The metallic pigments obtained are processed under conditions similar to those described in Example 5, to give magnetic tapes. A magnetic coating about 4μ thick is applied to a 20μ thick base film. As in Example 5, the tape width is 3.81 mm.

Since the conditions for carrying out measurements on such tapes have hitherto not formed the subject of Standard Specifications, the maximum output level at short wavelength (333 Hz) and long wavelength (8 kHz) are measured in comparison to average values obtained with gamma-$Fe_2O_3$ magnetic recording media. The measurements are carried out at a tape speed of 4.75 cm/sec. The recording current is increased, in accordance with the fact that the tapes have a higher coercive force than that of gamma-$Fe_2O_3$ tapes.

| Tape values: Pigments from Examples | 1 | 2 | A | B |
|---|---|---|---|---|
| $H_c$ (Oe) | 930 | 980 | 550 | 695 |
| Remanence (mT) in the preferred direction | 29.2 | 27.8 | 23.1 | 21.9 |
| Maximum output level at short wavelengths (dB) | +7 | +6.5 | +4 | +3.5 |
| Maximum output level at long wavelengths (dB) | +10 | +10 | +7.5 | +8 |
| Signal to noise ratio (dB) | 65 | 65.4 | 63.2 | 62.8 |

The comparative measurements show that a magnetic recording media containing metallic iron pigments which have been manufactured from goethite produced as described in Examples 1 and 2 exhibit improved properties compared to those manufactured with the goethite from Comparative Examples A and B, in respect of the maximum output level at both short and long wavelengths.

We claim:
1. In a process for manufacturing acicular γ-iron(II) oxide wherein an aqueous solution of an iron(II) salt is reacted with an aqueous solution of an alkali metal hydroxide and the resulting suspension of iron(II) hydroxide is oxidized with oxygen or oxygen-containing gases to give goethite, reducing the resulting goethite to magnetite and oxidizing the magnetite to acicular γ-iron(III) oxide, the improvement comprising: carrying out the oxidation of the iron(II) hydroxide suspension in three stages wherein in a first stage from 4 to 15% by weight of the amount of iron(II) present is oxidized in the course of from 0.4 to 5 hours, in a second stage from 60 to 85% by weight of the amount of iron(II) originally present in the suspension is oxidized over an additional period of from 1.5 to 6 hours by introducing 0.3 to 0.9 moles per hour of oxygen/gram atom of the iron contained in the suspension at the beginning of said second stage and gradually increasing the supply of oxygen during said second stage up to 0.7 to 1.5 moles per hour of oxygen/gram atom of iron at the end thereof; and in a third stage oxidizing the remaining iron(II) by introducing 1.5 to 2.5 moles of oxygen per hour per gram atom of iron contained in the suspension.

2. A process as set forth in claim 1, wherein, in the first stage, the suspension is oxidized by stirring in contact with the atmosphere.

3. A process as set forth in claim 1, wherein, in the first stage, from 6 to 12% by weight of the amount of iron(II) contained in the suspension are oxidized in the course of from 2 to 4 hours.

4. A process as set forth in claim 1, wherein the oxidation in the second stage is carried out in the course of from 2 to 5 hours.

5. A process as set forth in claim 1, wherein, at the beginning of the second stage, from 0.4 to 0.7 mole of oxygen per gram atom of the iron contained in the suspension is introduced, per hour, into the suspension and this amount of oxygen is increased to from 0.8 to 1.1 moles up to the end of the second stage.

6. A process as set forth in claim 1, wherein air is used as the oxygen-containing gas.

* * * * *

UNITED STATES PATENT AND TRADEMARK OFFICE
CERTIFICATE OF CORRECTION

PATENT NO. : 4,061,726
DATED : December 6, 1977
INVENTOR(S) : OHLINGER ET AL

It is certified that error appears in the above-identified patent and that said Letters Patent are hereby corrected as shown below:

In claim 1, line 26 of column 8, delete "$\gamma$-iron(II)" and substitute -- $\gamma$-iron(III) --.

Signed and Sealed this

Twenty-fourth Day of April 1979

[SEAL]

Attest:

RUTH C. MASON
Attesting Officer

DONALD W. BANNER
Commissioner of Patents and Trademarks